(12) United States Patent
Genzow et al.

(10) Patent No.: US 10,849,314 B2
(45) Date of Patent: Dec. 1, 2020

(54) METHOD FOR PREDICTING A SPECIFIC RESPIRATORY PATHOGEN

(71) Applicant: Boehringer Ingelheim Vetmedica GmbH, Ingelheim am Rhein (DE)

(72) Inventors: Marika Christine Genzow, Wiesbaden (DE); Charles Oliver Gomez-Duran, Gau-Algesheim (DE)

(*) Notice: Subject to any disclaimer, the term of this patent is extended or adjusted under 35 U.S.C. 154(b) by 0 days.

(21) Appl. No.: 16/348,368

(22) PCT Filed: Nov. 12, 2017

(86) PCT No.: PCT/EP2017/078972
§ 371 (c)(1),
(2) Date: May 8, 2019

(87) PCT Pub. No.: WO2018/091382
PCT Pub. Date: May 24, 2018

(65) Prior Publication Data
US 2020/0022337 A1  Jan. 23, 2020

(30) Foreign Application Priority Data
Nov. 15, 2016  (EP) .................................... 16002421

(51) Int. Cl.
| | |
|---|---|
| *A01K 29/00* | (2006.01) |
| *A61B 7/00* | (2006.01) |
| *G10L 17/26* | (2013.01) |
| *G10L 21/0208* | (2013.01) |
| *G10L 25/66* | (2013.01) |

(52) U.S. Cl.
CPC ............ *A01K 29/005* (2013.01); *A61B 7/003* (2013.01); *G10L 17/26* (2013.01); *G10L 21/0208* (2013.01); *G10L 25/66* (2013.01)

(58) Field of Classification Search
CPC ........ A01K 1/00; A01K 29/005; A01K 29/00; A61B 7/003; G10L 17/26; G10L 21/0208; G10L 25/66; G10L 25/03
See application file for complete search history.

(56) References Cited

U.S. PATENT DOCUMENTS

| | | | | |
|---|---|---|---|---|
| 5,197,490 | A * | 3/1993 | Steiner ................. | A61B 5/0017 600/484 |
| 6,228,037 | B1 * | 5/2001 | Derksen ................. | A61B 7/003 600/529 |
| 6,520,924 | B2 * | 2/2003 | Lee .......................... | A61B 7/00 600/485 |
| 8,915,215 | B1 * | 12/2014 | Helgeson ............... | A01K 45/00 119/421 |
| 9,164,081 | B2 * | 10/2015 | Van Der Tol ........ | G01N 33/497 |
| 10,226,225 | B2 * | 3/2019 | Rodriguez-Villegas ..................... A61B 5/0022 |

(Continued)

FOREIGN PATENT DOCUMENTS

| | | | |
|---|---|---|---|
| EP | 2783629 | 10/2014 | |
| EP | 2783629 A1 * | 10/2014 | ........... A61B 5/0823 |

(Continued)

*Primary Examiner* — Ryan W Sherwin
(74) *Attorney, Agent, or Firm* — Steffan Finnegan (57) ABSTRACT

The invention relates to a method carried out by a processor for predicting a specific respiratory pathogen in a group of farm animals, which method comprises monitoring the sounds generated by said farm animals.

19 Claims, 6 Drawing Sheets

(56) References Cited

U.S. PATENT DOCUMENTS

| | | | | |
|---|---|---|---|---|
| 2003/0205208 | A1* | 11/2003 | Bar-Shalom | A01K 29/005 |
| | | | | 119/859 |
| 2004/0133079 | A1* | 7/2004 | Mazar | A61B 5/0031 |
| | | | | 600/300 |
| 2006/0074334 | A1* | 4/2006 | Coyle | A61B 7/003 |
| | | | | 600/529 |
| 2008/0275349 | A1* | 11/2008 | Halperin | A61B 5/447 |
| | | | | 600/484 |
| 2009/0216127 | A1* | 8/2009 | Gavriely | A61B 5/053 |
| | | | | 600/453 |
| 2009/0301402 | A1* | 12/2009 | Devine | A01K 1/00 |
| | | | | 119/447 |
| 2012/0302898 | A1* | 11/2012 | Zhang | A61B 5/0823 |
| | | | | 600/484 |
| 2013/0150744 | A1* | 6/2013 | Brattain | A61B 7/003 |
| | | | | 600/529 |
| 2015/0327518 | A1* | 11/2015 | Han | A01K 29/00 |
| | | | | 348/143 |

FOREIGN PATENT DOCUMENTS

| | | |
|---|---|---|
| JP | 2011217934 | 11/2011 |
| WO | 2008152433 A1 | 12/2008 |
| WO | 2014123732 A1 | 8/2014 |

* cited by examiner

METHOD FOR PREDICTING A SPECIFIC RESPIRATORY PATHOGEN

CROSS-REFERENCE TO RELATED APPLICATIONS

This application claims the benefit from the priority of European patent application EP 16002421.2 filed on Nov. 15, 2016; the entire content of this application is hereby incorporated by reference.

BACKGROUND OF THE INVENTION

1. Technical Field

The invention relates to a method carried out by a processor for predicting a specific respiratory pathogen in a group of farm animals comprising recording the sounds; converting the analog recording into digital data; filtering off background noises from sounds caused by respiratory distress; comparing the resultingrespiratory distress index (RDI) pattern with a stored table containing data of different RDI patterns generated by several different respiratory pathogens; and reporting the respiratory pathogen, which corresponds to the matching RDI patterns.

Furthermore, the invention relates to a non-transitory processor readable medium having stored thereon processor executable instructions configured to cause a processor to perform the method according to the invention, a computing device to carry out the method according to the invention, and a kit of parts for carrying out the inventive method comprising such a computing device and at least one microphone.

2. Background Information

In recent years, several factors have stressed traditional livestock farming. Firstly, the global meat demand has grown extremely as the world population continues to grow. Furthermore, income per capita is increasing, particularly in the upcoming industries like the BRIC-countries. This enables massive new groups of people to consume meat. Another trend specific to consumers in developed countries is the augmented concern towards ethical and environmentally friendly meat production. Additionally, there is a clear need for a reduction in the use of antibiotics in intensive livestock production (Aarestrup, F. 2012, Nature 486, 465-466; Kimman, T., Smits, M., Kemp, B., Wever, P., and Verheijden, J. 2010. Banning Antibiotics, Reducing Resistance, Preventing and Fighting Infections: White Paper on Research Enabling an Antibiotic-free' Animal Husbandry. Wageningen Academic UR).

Livestock farming may be regarded as a process control technology, in which context the Precision Livestock Farming (PLF) is often used (Berckmans, D. 2006, in *Livestock Production and Society*, R. Geers, and F. Madec, eds. Wageningen Academic Publishers. 51-54).

Different kinds of sensors are employed to facilitate PLF in a practical setup, e.g., cameras (CCTV, infra-red, 3D, thermal . . . ), accelerometers, flow meters, etc. A particularly interesting type of PLF techniques uses microphones to capture sound. Sound contains a lot of useful information about the animal and its environment (communication, health, welfare).

Recently, a number of examples of sound-based PLF-technology have emerged in different species. Moura et al. showed how thermal (dis-)comfort can be monitored in broilers based on sound analysis (Moura, D. J. de, Nääs, I. de A., Alves, E. C. de S., Carvalho, T. M. R. de, do Vale, M. M., and Lima, K. A. O. de 2008, Sci. Agric. 65,438-443), while Aydin et al. demonstrated the monitoring of broiler feed intake by pecking sounds (Aydin, A., Bahr, C., Viazzi, S., Exadaktylos, V., Buyse, J., and Berckmans, D. 2014. Comput. Electron. Agric. 101, 17-23). Hillman et al. used acoustic monitoring of pigs for the detection of thermal (dis-) comfort (Hillmann, E., Mayer, C., Schön, P.-C., Puppe, B., and Schrader, L. 2004, Appl. Anim. Behav. Sci. 89, 195-206).

Van Hirtum et al. first developed algorithms to discriminate pathological from non-pathological pig coughs (Van Hirtum, A. 2002. The acoustics of coughing. PhD Thesis. KU Leuven. Leuven, Belgium). Ferrari et al. did a characterisation of pig cough sounds using time and frequency-derived parameters (Ferrari et al., 2008).

The link between automatically measured cough and anomalies in respiratory porcine behaviour has been validated extensively in several field trials (Finger, G., Hemeryck, M., Gomez-Duran, O., and Genzow, M. 2014, in *Proceedings of the 23rd IPVS Congress*, Cancun, Mexico. 207-208; Genzow, M., Gomez-Duran, O., Hemeryck, M., and Finger, G. 2014a, in *Proceedings of the 23rd IPVS Congress*, Cancun, Mexico. 212-213; Genzow, M., Gomez-Duran, O., Strutzberg-Minder, K., Finger, G., and Hemeryck, M. 2014b, in *Proceedings of the 23rd IPVS Congress*, Cancun, Mexico. 205-206; Berckmans, Hemeryck, M., Berckmans, D., Vranken, E., van Waterschoot, T., 2015 in *Int. Symp. on Animal Environ. & Welfare* Oct. 23-26, 2015, Chongqing, China).

The European patent application EP 2783 629 A1 discloses a method and/or system for monitoring the sounds of a group of farm animals with a microphone connected with a computing device, in which the computing device records the sounds made by the animals, performs filtering operations to filter off background noises, counting the number of sounds caused by respiratory distress over a certain period of time and alerts an operator, if the registered number of sounds caused by respiratory distress exceeds a given value.

The International patent application WO 2008/152433 teaches a method and/or system for combining the respiratory status (e.g. amount and type of cough) with the localization of organisms having the respiratory status in real time. Furthermore, it suggests that the type of cough may be recognized utilizing Auto Regression analysis.

However, the hitherto described methods are not capable to predict the pathogen, which causes the respiratory distress of the animals monitored. Accordingly, there is a high demand for a measurement of sounds caused by respiratory distress in farm animals, which can be used as a diagnostic tool to predict the pathogen causing the distress. The problem underlying the present invention was to provide a method to measure sounds caused by respiratory stress in farm animals, which allows predicting the pathogen causing the respiratory stress.

It has now been found, surprisingly that each respiratory pathogen creates a distinctive pattern of the respiratory distress index (RDI) being the number of sounds caused by respiratory distress per single farm animal within a pre-defined period. The problem underlying the present invention has been solved by a method wherein the pattern of the RDI is measured, monitored and stored over a period of time and compared with a table in which different RDI patterns are stored.

BRIEF SUMMARY OF THE INVENTION

Accordingly, the invention relates to a method for predicting a specific respiratory pathogen in a group of farm animals, comprising the following steps:
- a) recording the sounds generated in the group of the farm animals over a certain period of time;
- b) converting the analog recording into digital data;
- c) performing filtering operations, which filter off background noises from sounds caused by respiratory distress;
- d) counting the number of sounds caused by respiratory distress during the recordal time;
- e) calculating the respiratory distress index (RDI) as being the number of sounds caused by respiratory distress within a pre-defined period of time, optionally corrected by the number of farm animals within the reach of each microphone;
- f) monitoring and storing the pattern of the RDI over a period of time;
- g) comparing data of the resulting RDI pattern with a stored table containing data of different RDI patterns generated by several different respiratory pathogens; and
- h) reporting the respiratory pathogen, which corresponds to the matching RDI patterns, wherein the steps b) to h) are carried out by a processor.

The invention further relates to a non-transitory processor readable medium having stored thereon processor executable instructions configured to cause a processor to perform each of the inventive method steps b) to h).

Furthermore, the invention relates to a computing device for predicting a specific respiratory pathogen in a group of farm animals, the computing device comprising means to carry out the method steps b) to h) according to the invention.

In addition, the invention relates to a kit of parts for carrying out each of the method steps according to the invention consisting essentially of
- (A) an inventive computing device;
- (B) at least one microphone connectable with said computing device (A); and
- (C) optionally an information booklet providing instruction for the installation and utilization of (A) and (B).

BRIEF DESCRIPTION OF THE DRAWINGS

The accompanying drawings illustrate embodiments of the invention, and, together with specification, including the general description above and the detailed description, which follows, serve to explain the features of the present invention.

DETAILED DESCRIPTION OF THE INVENTION

The term "respiratory pathogen" as used hereinabove or hereinbelow in its oldest and broadest sense is anything that can produce a respiratory disease. It embraces both infectious agents such as viruses, bacteria, prions, fungi, or even other micro-organisms; and non-infectious agents such as chemical gaseous agents including ammonia, hydrogen sulfide, carbon dioxide and methane, organic dust originating from feed, fecal particles or dander, endotoxins including coliforms in fecal dust, and smoke.

The term "predicting pathogens" as used hereinabove or hereinbelow means that the pattern of the RDI values obtained in a specific farm, stable or part of a stable are compared with a library or table of RDI patterns obtained from monitoring farm animals, which had been infected by a specific pathogen. If the actual pattern matches with one of the stored pathogen specific patterns, it can be predicted, that at least one animal in the monitored group is infected with the matching pathogen.

The term "predicting pathogens" does not include the attribution of the deviation to a particular clinical picture on a specific animal, i.e. the deductive veterinary decision. Nevertheless, it is a helpful tool for the veterinarian which may form part of such decision.

The term "pathogen specific RDI pattern" as used hereinabove or hereinbelow means the pattern of the RDI values caused by a specific respiratory pathogen. It includes the form of the curve of the these RDI values with the time, the steepness of increase of the RDI values as well as the area under the curve. All these features are pathogen-specific and are stored in the table of the computing device. Such a table had been established previously by simultaneously measuring the sounds in farm animals, calculating the RDI values and diagnosing the correlating pathogen causing the respiratory distress sounds.

The term "sounds of respiratory distress" as used hereinabove or hereinbelow includes all kinds of sounds that farm animals make due to respiratory disorders or diseases including but not limited to coughing, sneezing, harrumphing, and wheezing.

The term "farm animals" as used hereinabove or hereinbelow includes all kinds of animals which are maintained in a farm for production of animal product or for leisure, such as, horses, dogs, donkeys, ostriches and minks, in particular pigs, cattle, horses, and poultry.

The term "processor" as used hereinabove or hereinbelow means a computing device such as an industrial computer, personal computer (PC), laptop, or tablet, which may be located within the farm, stable, or section of a stable, or is connected via data transfer means with a microphone located within the farm, stable, or section of a stable.

The term "connected" or "connectable" used hereinabove or hereinbelow with respect to the relationship of the microphone and the computing device is intended to include any direct linkage by a suitable cable or wire, but also any wireless connection such as infrared, Bluetooth or WLAN.

The term "computing device" as used hereinabove and hereinbelow means not only a processor in a housing connected to the microphone, but also includes a system comprising a device that first receives the acoustic data from the microphone, then stores such data in a processor readable medium and later transmits it to a processor.

The term "processor readable medium" as used hereinbefore or hereinbelow includes any medium that can be used to store digital data including but not limited to internal or external hard drives, SSD drives, SDI cards, storage clouds, CDs, DVDs, USB sticks, floppy discs, and magnetic tapes.

The term "comparing data of the resulting RDI pattern" as used hereinbefore or hereinbelow includes the comparison of pathogen specific or library with the actual RDI pattern obtained from a group of the farm animals. In such a comparison the total number of RDIs or the area under the curve, the number of RDI maxima, the time to reach the first and any following maximum, the time of decline from any maximum of the actual RDI pattern obtained from a group of the farm animals will be compared with the corresponding features of the pathogen specific RDI patterns stored in the table. The processor will determine the difference between these features of the actual RDI pattern and the RDI patterns stored in the table and indicate the pathogen, for which this difference forms a minimum.

The following methods are preferred embodiments of the present invention:

A method, wherein
  (a) the farm animals are selected from the group consisting of cattle, pigs, and poultry, in particular growing/fattening pigs or breeding pigs;
  (b) the respiratory pathogens of the stored table have been verified by diagnostic one or more methods, preferably by a pen-based oral fluid sampling combined with an enzyme-linked immunosorbent assay (ELISA) or polymerase chain reaction (PCR) and/or blood serum testing.
  (c) the respiratory pathogen is selected from the group consisting of one or more bacteria, mycoplasmas and viruses, preferably from the group consisting of *Acinetobacter, Actinobacillus*, in particular *Actinobacillus pleuropneumiae* (APP), *Arcanobacterium, Bordetella, Haemophilus, Klebsiella, Pasteurella, Salmonella, Streptococcus, M. hyorhinis, M. hyopneumoniae,* Swine Influenza, Porcine Reproductive and Respiratory Syndrome to (PRRS) virus, Respiratory coronavirus, Porcine circovirus type 2 (PCV2), Porcine cytomegalovirus, Aujeszky's Disease, Classical swine fever and African swine fever, in particular APP, *M. hyopneumoniae*, Swine Influenza, PRRS, and PCV2, most preferably Swine Influenza;
  (d) the respiratory pathogen is selected from the group consisting of non-infectious agents such as chemical gaseous agents including ammonia, hydrogen sulfide, carbon dioxide and methane, organic dust originating from feed, fecal particles or dander, endotoxins including coliforms in fecal dust, and smoke
  (e) the sound caused by respiratory distress is sneezing and/or coughing;
  (f) the sounds generated in the group of the farm animals are recorded continuously over a period of at least two weeks, preferably 1 to 12 months;
  (g) in step a) the noises produced by 1 to 1000 farm animals are recorded using 1 to 4 microphones, depending on the size of the monitored farm animals, in preferably 5 to 200 pigs, 10 to 1000 chicken, or 1 to 50 cows.
  (h) in step c) the stored data generated from the sounds produced by a group of healthy farm animals is used to filter off the background noise.
  (i) in step e) the RDI is the number of sounds caused by respiratory distress per single farm animal within 5 to 48, preferably 12 to 36, in particular about 24 hours, in another preferred embodiment during hours of low activity in the farm such as the night time.
  (j) in step g) the stored table of respiratory pathogens comprises 1 to 10, preferably 2 to 6 different respiratory pathogens, in particular APP, *M. hyopneumoniae*, Swine Influenza, PRRS and PCV2, and their corresponding RDI patterns.
  (k) in step h), the processor produces a report indicating one or more RDI values that exceeded the threshold RDI value and/or transmits such report to the stockman or veterinarian health professional, who is in charge of the group of farm animals.

The various embodiments will be described in detail with reference to the accompanying drawings. Where possible the same reference numbers will be used throughout the drawings to refer to the same or like parts. References made to particular examples and implementations are for illustrative purposes, and are not intended to limit the scope of the claims.

The hardware used to capture the sounds was a' SOMO+ sound recording device of SoundTalks BV, Belgium. The phantom-powered (i.e., DC electric power is transmitted through the microphone cables to operate the microphones that contain active electronic circuitry) microphones were connected in a balanced way. This permits the use of long microphone cables, with limited susceptibility to noise. The microphones were typically centered with respect to the position of the animals that were monitored (e.g., pigpen). The microphones were fixed at a height of 2 meters to be close enough to animals, yet not too close for the animals to reach them. Recordings were continuous (24/24, 7 d/w) in files of 5 minutes duration. The recording parameters were set to 16 signed integer bit resolution, with a sampling rate of 22.05 kHz (standard WAV file format). The embedded sound card was fanless and protected from the harsh environment by a sealed enclosure. The microphone was protected from the environment by a thin and flexible cover, designed to not interfere with the sound acquisition in the frequency range of interest, i.e., from 1 kHz to 5 kHz. The equipment, much like similar PLF technologies, was subject to a range of robustness-related issues typical in the farm environment.

In parallel to the sound monitoring and RDI calculations various diagnostic tests such as (discrete) saliva or serum drawings were carried out. The saliva and serum drawings were tested for *Actinobacillus pleuropneumiae* (APP), Swine Influenza Virus (SIAV), *Mycoplasma hyopneumoniae* (*M. Hyo*) and Porcine reproductive and respiratory syndrome virus (PRRSV). The diagnostic results showed that the patterns of the RDI values are specific to the pathogen causing the respiratory distress.

The term "swine influenza virus (SIAV)" is known by the person skilled in the art. The term swine influenza virus refers to a type A or type C influenza virus from the family orthomyxovirus that causes swine influenza. While orthomyxovirus has three groups: type A, type B, and type C, only type A and type C influenza viruses infect pigs. Preferably, the swine influenza virus is a Swine Influenza A virus. Subtypes of swine influenza virus include H1N1, H1N2, H3N2, and H3N1. H9N2 and H5N1 can also be found in pigs.

Alternatively, the animals will be infected with a specific pathogen and the sounds caused by the respiratory distress is monitored over a certain time period after the infection and the resulting RDI pattern is used, as the pathogen-specific RDI pattern for said pathogen.

The patterns of these pathogen-specific RDI values are stored as a table or library in the computing device.

Figure 1:
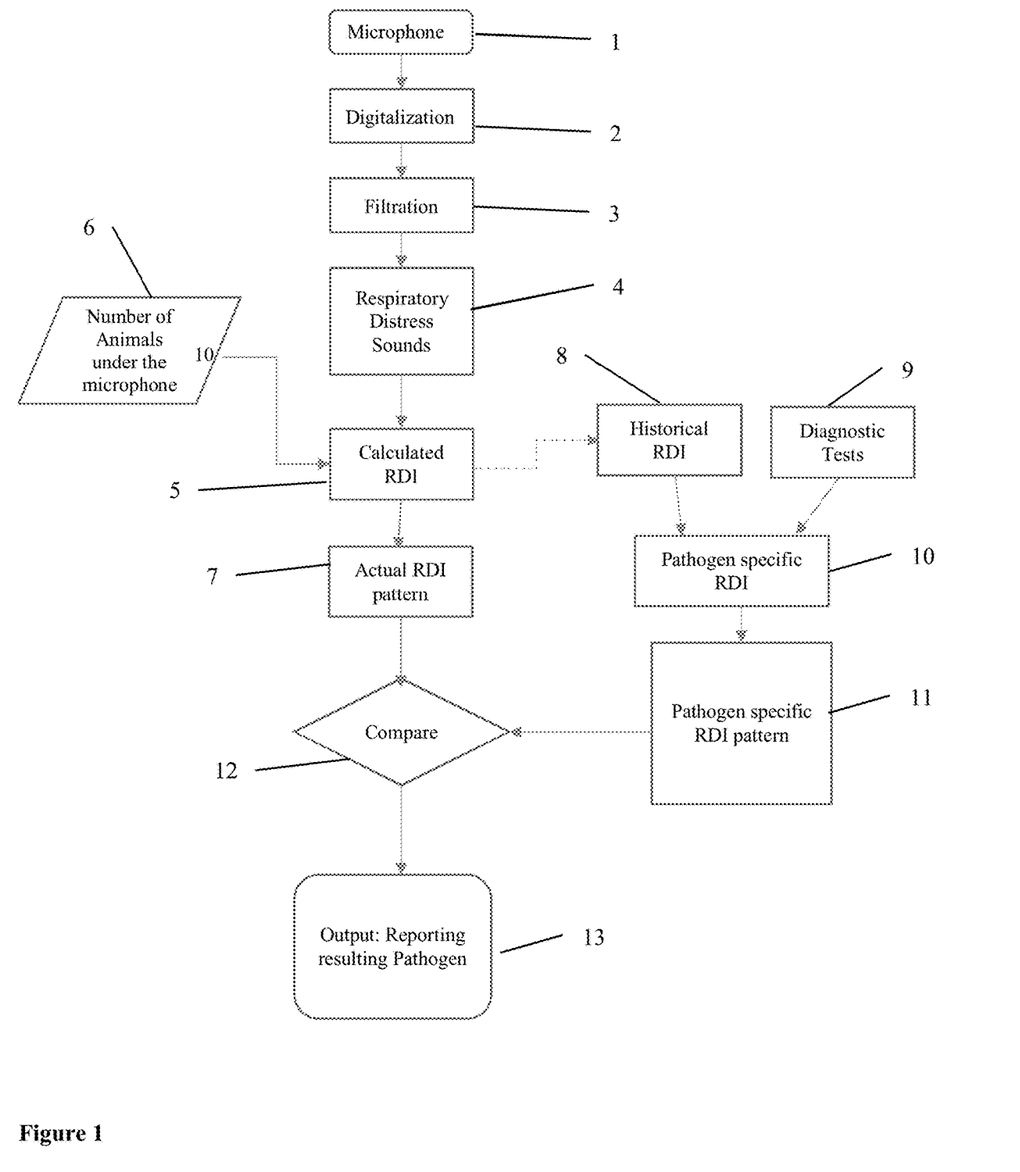
FIG. 1 is a process flow diagram illustrating an embodiment of the method according to the invention.

The process flow diagram of FIG. 1 shows how one or more microphones (1) first pick up the sounds that occur in a farm, stable or part of the stable. The sounds are then converted from an analogue to a digital signal by an analogue-to-digital convertor (2). After digitalization, different filtering techniques (3) are applied to separate respiratory distress sounds from all other sounds that are captured by the microphone(s). The other sounds include both stationary background sounds like e.g. fan noise or feeding line noise, and also transient sound events that are not related to respiratory distress, such as e.g. knocks or screams. The respiratory distress index (RDI) (5) is then calculated as the number of sounds (4) caused by respiratory distress within a pre-defined period of time, scaled with the number of captured farm animals (6), i.e. those in the vicinity of the microphone(s) (1) as shown in FIG. 3A. The RDI values are stored over a period of time and a series of historical RDI values (8), which are accompanied by diagnostic testing to verify the pathogen causing the respiratory distress sounds, serve as input for the determination of the pathogen-specific RDI values (10). The patterns of these pathogen-specific values (11) are stored in a table of the computing device. The actual calculated RDI pattern (7) is then compared with the stored patterns of these pathogen-specific RDI values (11). This comparison (12) serves as the output of the method (13), reporting the resulting pathogen as well as the pattern of the RDI values.

Figure 2:
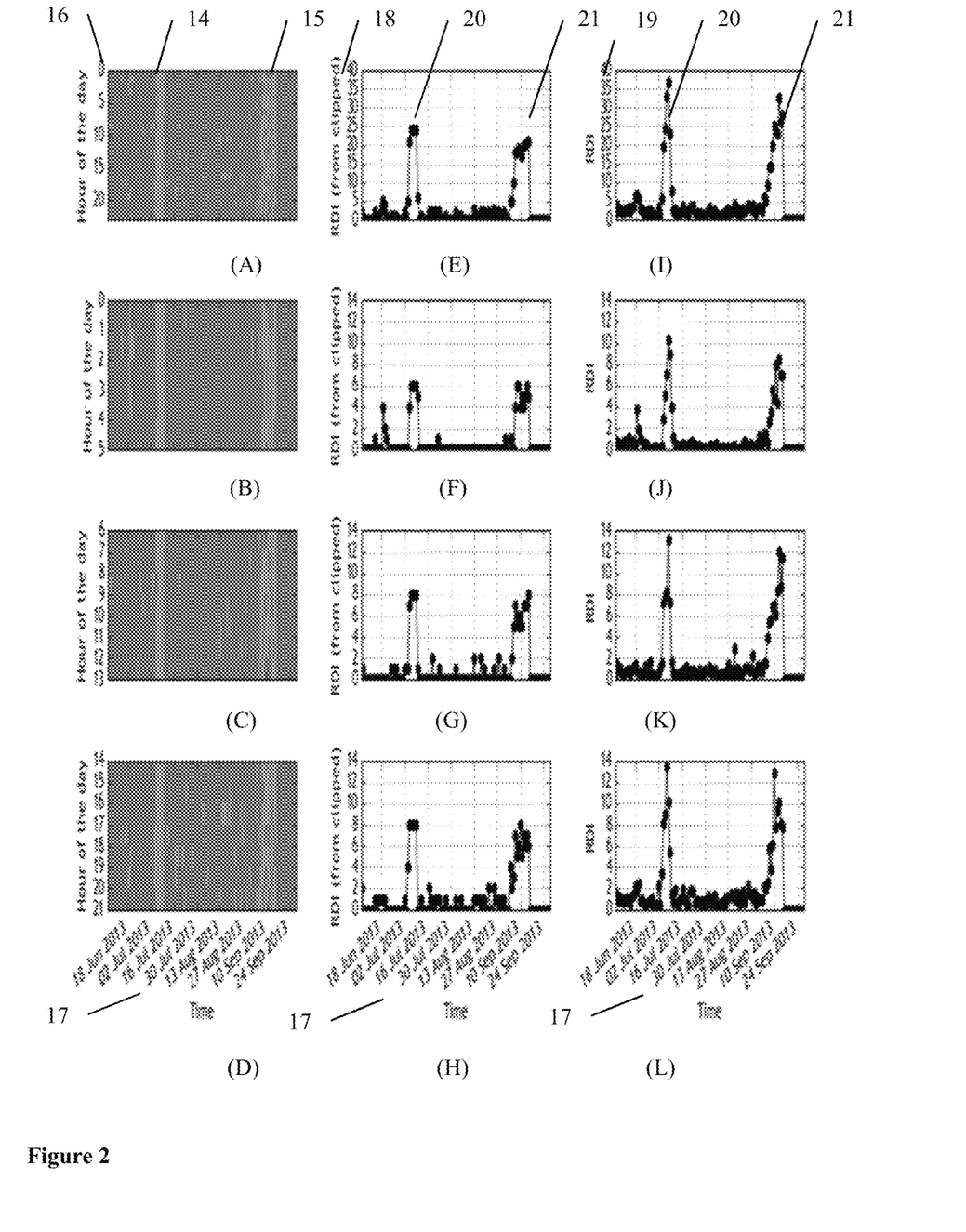
FIG. 2 illustrates the resulting output data showing RDI pattern caused by Swine Influenza Virus.

FIG. 2 shows an example of the method according to the invention with pigs that were infected with Swine Influenza Virus. The sounds of the animals were monitored between June and October 2013. The arrangement of the sound monitoring system in farm stables was as shown in FIG. 4B.

FIG. 2A shows the intensity of respiratory distress sounds as in form of the lighter bars (14, 15) during each day within 24 hours. The ordinate (16) indicates the hours of the day and the X-axis (17) shows the dates of the monitoring.

FIGS. 2B to 2D show the intensity of respiratory distress sounds as in form of the lighter bars (14, 15) during different times of each day, i.e. from 0 to 5 o'clock (FIG. 2B), from 6 to 13 o'clock (FIG. 2C) and from 14 to 21 o'clock (FIG. 2D). The ordinate (16) indicates the hours of the day and the X-axis (17) shows the dates of the monitoring period.

FIG. 2E to FIG. 2H indicate the corresponding RDI (from clipped) values (18) and FIG. 2I to FIG. 2L indicate the corresponding RDI values (19).

In this example, it is clear that there was a steep increase and decrease of RDI values between Jul. 3 and 10, 2013 (20) and a second steep increase between Sep. 3 and 14, 2013 (21). The highest RDI value is reached already after less than about 5 days. Such narrow, steep peaks are typical for swine influenza. The same is true for the comparably short duration and the small area under the curve.

The pre-determined pathogen-specific RDI pattern of SIAV is stored in the computing device and the actually monitored RDI patterns are compared therewith by said computing device, which indicates if the actually monitored RDI pattern matches with the stored SIAV RDI pattern and indicates SIAV as the pathogen that caused the actual RDI pattern.

Figure 3:
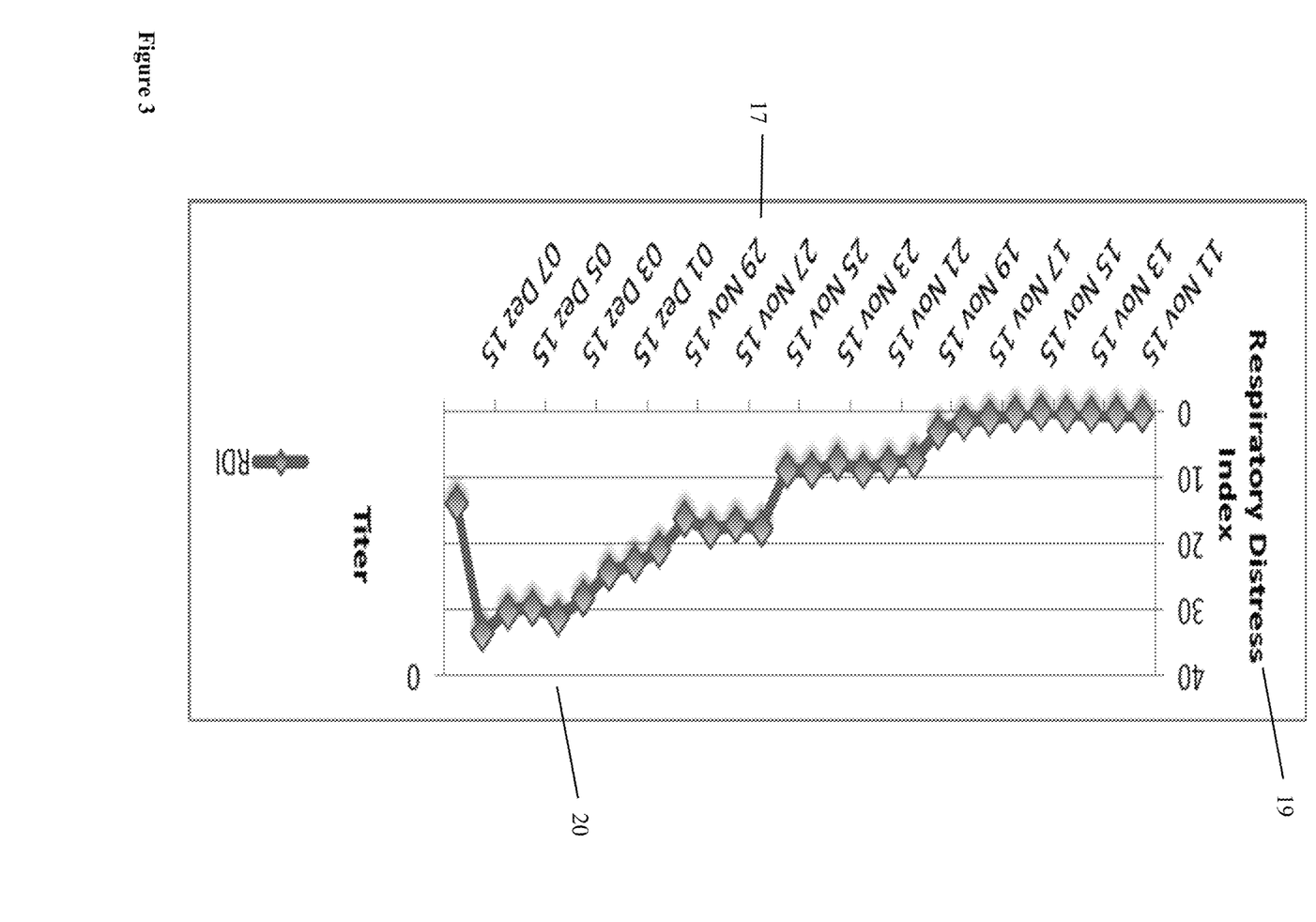
FIG. 3 illustrates the resulting output data showing RDI pattern caused by *Mycoplasma hyopneumoniae*.

FIG. 3 shows an example of the method according to the invention with pigs that were infected with Mycoplasma hyopneumoniae indicating the corresponding RDI values (19). The sounds of the animals were monitored between November 11 and Dec. 8, 2015 (17). The arrangement of the sound monitoring system in farm stables was as shown in FIG. 6B.

In this example, it is clear that there was a very slow increase between November 18 and December 7 (20). The highest RDI value is reached only after about 19 days. Such extremely broad peaks are typical for *Mycoplasma hyopneumoniae*. The same is true for the very long duration and the large area under the curve.

The pre-determined pathogen-specific RDI pattern of Mycoplasma hyopneumoniae is stored in the computing device and the actually monitored RDI patterns are compared therewith by said computing device, which indicates if the actually monitored RDI pattern matches with the stored Mycoplasma hyopneumoniae RDI pattern and indicates Mycoplasma hyopneumoniae as the pathogen that caused the actual RDI pattern.

Figure 4:
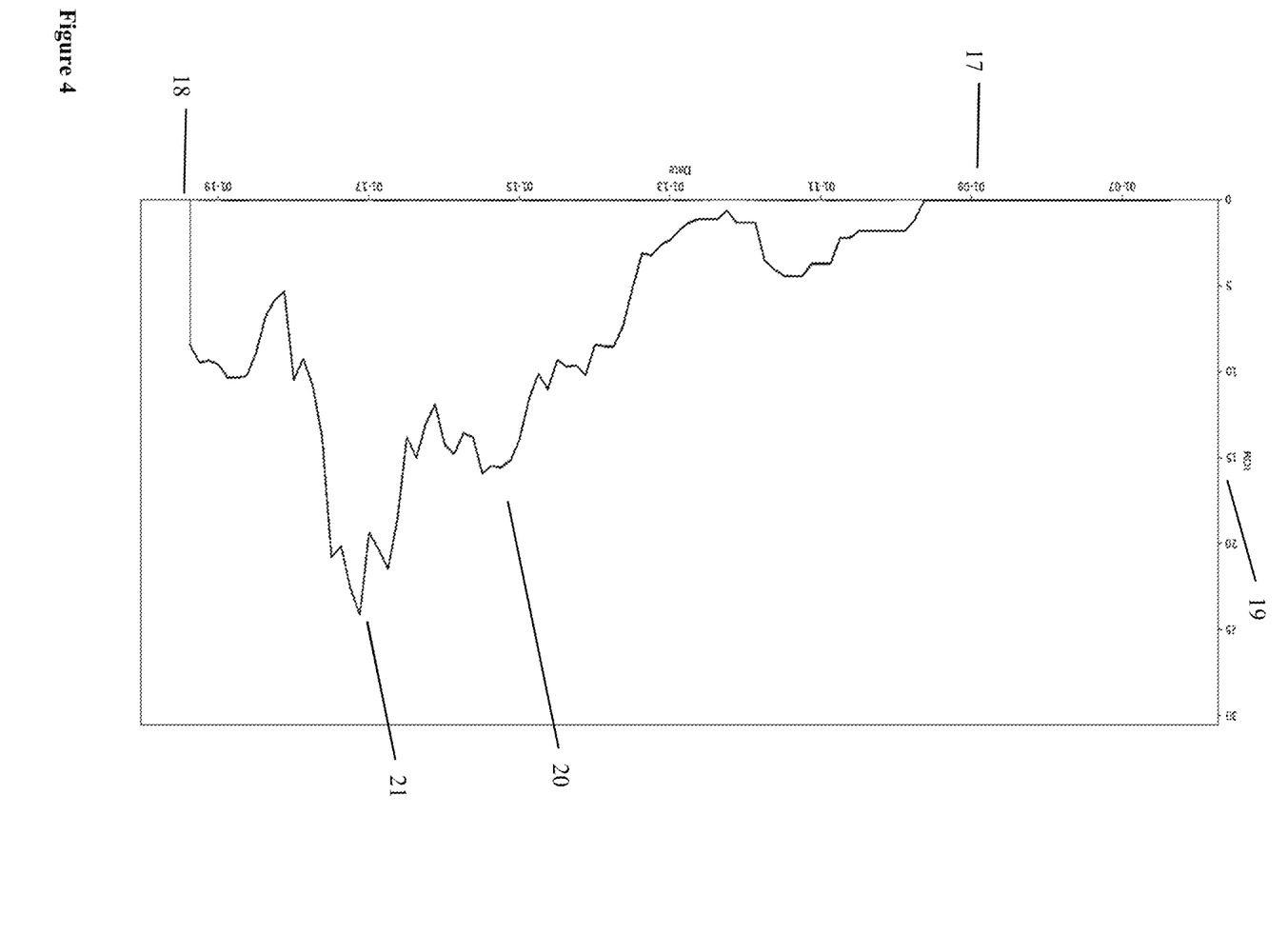
FIG. 4 illustrates the resulting output data showing RDI pattern caused by *Actinobacillus pleuropneumiae* (APP).

FIG. 4 shows an example of the method according to the invention with pigs that were infected with *Actinobacillus pleuropneumiae* (APP) indicating the corresponding RDI values (19). The sounds of the animals were monitored between January 9 and 20 (17, 18). Initially the trial was carried out with ten pigs. The animals were infected with APP on January 12.

In this example, it is clear that there was a very steep increase between January 12 and 15 (20). The highest RDI value is already reached on January 17 (21). Such steep curves with two strong peaks within 2-3 consecutive days are typical for APP.

The pre-determined pathogen-specific RDI pattern of APP is stored in the computing device and the actually monitored RDI patterns are compared therewith by said computing device, which indicates if the actually monitored RDI pattern matches with the stored APP RDI pattern and indicates APP as the pathogen that caused the actual RDI pattern.

Figure 5:
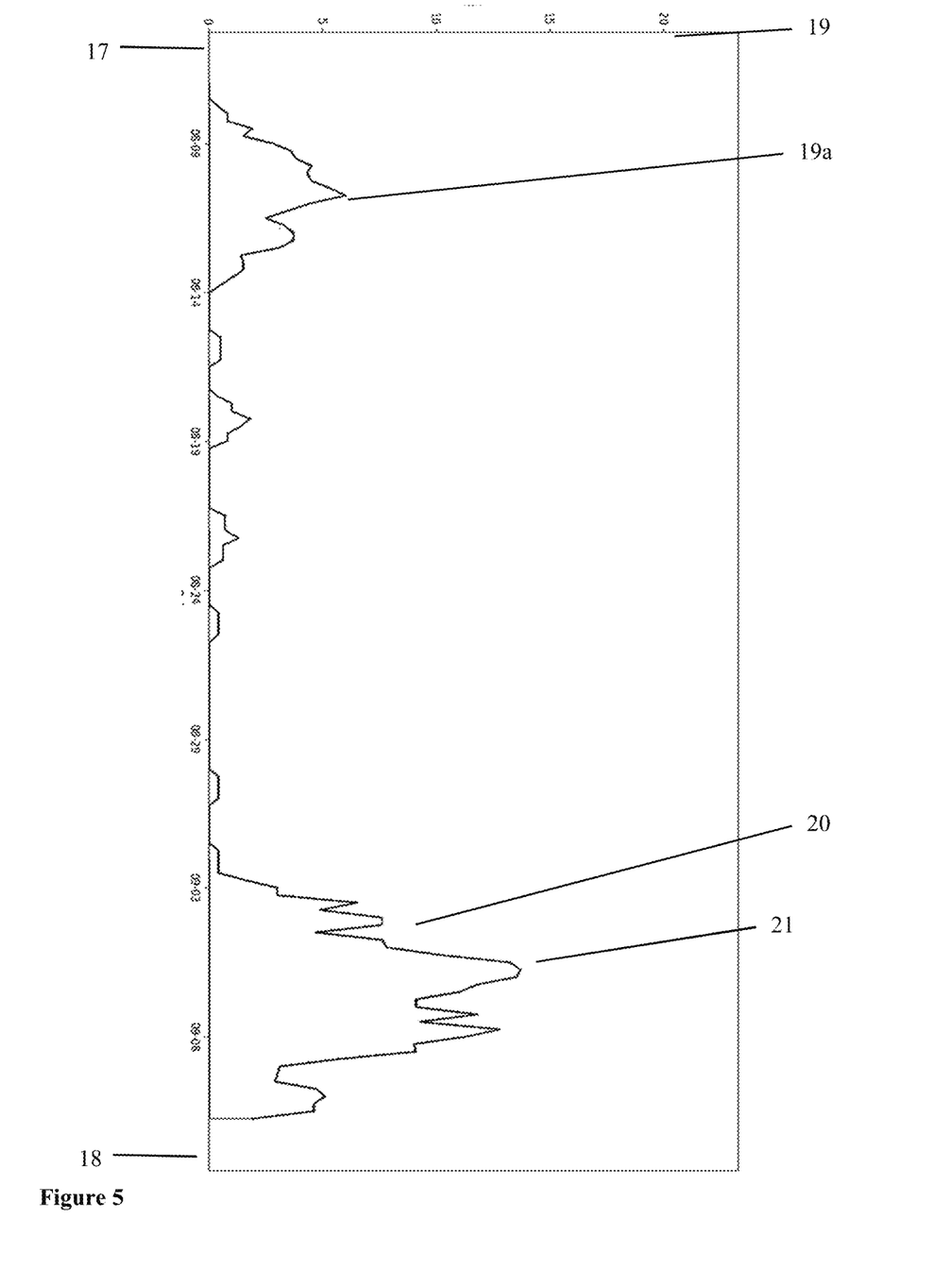
FIG. 5 illustrates the resulting output data showing RDI pattern caused by Porcine Reproductive and Respiratory Syndrome (PRRS) virus.

FIG. 5 shows an example of the method according to the invention with pigs that were infected with Porcine Reproductive and Respiratory Syndrome (PRRS) virus indicating the corresponding RDI values (19). The sounds of the animals were monitored between August 7 and September 11 (17, 18). Initially the trial was carried out with ten pigs, 4 weeks of age. The animals were infected with PRRS on August 7. The slightly enhanced RDI values between August 8 and 14 (19a) were not caused by PRRS, but by an endemic *Mycoplasma hyopneumoniae* infection.

In this example, it is clear that almost no respiratory symptoms from the PRRS infection could be detected between August 15 and September 2, but a steep increase of the RDI values began on September 3 (20). The highest RDI values were reached between September 4 and 8 (21). Such steep curves with two to three strong peaks within 2-3 consecutive days after a long during time without respiratory symptoms are typical for PRRS.

Upon deletion of the RDI values caused by the endemic Mycoplasma hyopneumoniae infection (19a), the pre-determined pathogen-specific RDI pattern of PRRS is stored in the computing device and the actually monitored RDI patterns are compared therewith by said computing device, which indicates if the actually monitored RDI pattern matches with the stored PRRS RDI pattern and indicates PRRS as the pathogen that caused the actual RDI pattern.

Figure 6:
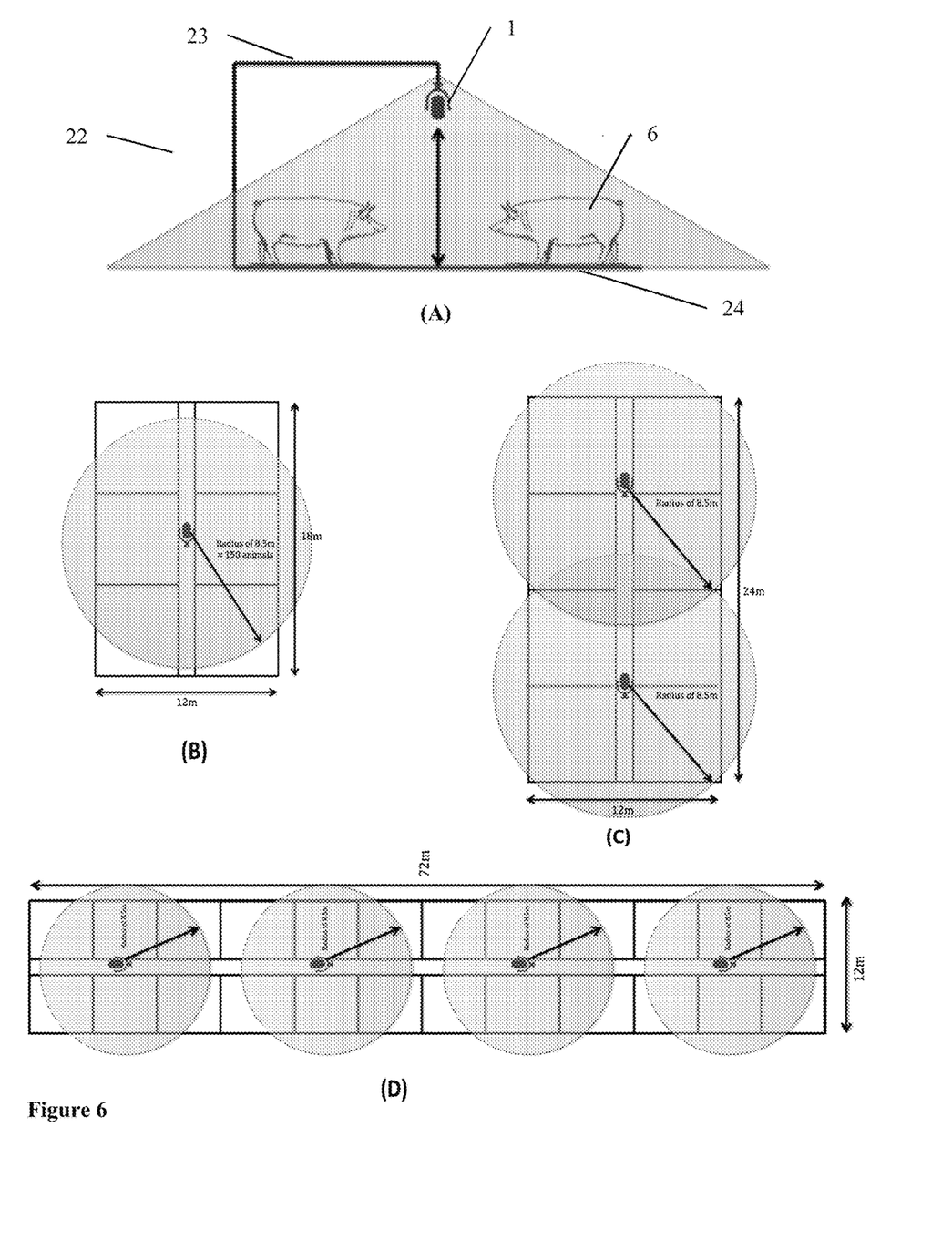
FIG. 6 illustrates an exemplary arrangement of the sound monitoring system in a farm stable.

FIG. 6 illustrates different exemplary arrangements of the sound monitoring system in farm stables. FIG. 6A shows a schematic cross-section of a pig stable (22), in which the microphone (1) is mounted at the ceiling (23) of the stable in a height of about 2 meters. The sounds made by all animals (6) within a radius of about 7 to 9 meters on the ground (24) are within the reach of the microphone.

FIG. 6B shows a top view of six pigpens with a length of about 6 meters and a width of about 5 meters. The total pig population is 225. One microphone records the sounds made by about 75% of the animals.

FIG. 6C shows a top view of eight pigpens with a length of about 6 meters and a width of about 5 meters. The total pig population is 320. Two microphones record the sounds made by all the animals.

FIG. 6D shows a top view of twenty-four pigpens with a length of about 6 meters and a width of about 5 meters. The total pig population is 1000. Four microphones record the sounds made by about 75% of the animals.

The preceding description of the disclosed embodiments is provided to enable a person skilled in the art to make or use the present invention. Various modifications of these embodiments will be readily apparent to those skilled in the art, and the general principles defined herein may be applied to other embodiments without departing from the spirit or scope of the invention. Thus, the present invention is not intended to be limited to the embodiments shown herein but to be accorded the widest scope consistent with the following claims and the principles and features disclosed herein.

The invention claimed is:

1. A method for predicting a specific respiratory pathogen in a group of farm animals, comprising the following steps:
    a) continuously contact-free recording the externally expressed respiratory sounds caused by respiratory distress comprising coughing, sneezing, harrumphing and wheezing generated collectively by the group of the farm animals over a certain period of time;
    b) converting the analog recording into digital data;
    c) performing a filtering operation, which filters off background noises from sounds caused by respiratory distress;
    d) counting the number of sounds caused by respiratory distress during the recording time;
    e) calculating the respiratory distress index (RDI) as being the number of sounds caused by respiratory distress within a pre-defined period of time, optionally corrected for the number of farm animal within the reach of each microphone;
    f) monitoring and storing a pattern of the RDI over a period of time;
    g) comparing data of the resulting RDI pattern with a stored table containing data of different RDI patterns generated by several different respiratory pathogens; and
    h) reporting the respiratory pathogen, which corresponds to the matching RDI patterns, wherein the steps c) to h) are carried out by a processor.

2. The method of claim 1, wherein the farm animals are selected from the group consisting of cattle, pigs, horses, and poultry.

3. The method of claim 1, wherein the respiratory pathogens of the stored table have been verified by diagnostic one or more methods, preferably by a pen-based oral fluid sampling combined with an enzyme-linked immunosorbent assay (ELISA) or polymerase chain reaction (PCR) and/or blood serum testing.

4. The method according to claim 1, wherein the respiratory pathogen is an infectious agent selected from the group consisting of one or more bacteria, mycoplasmas and viruses or a non-infectious agent selected from the group consisting of chemical gaseous agents, organic dust, endotoxins, and smoke.

5. The method according to claim 1, wherein the respiratory pathogen is selected from the group consisting of *Acinetobacter, Actinobacillus, Arcanobacterium, Bordetella, Haemophilus, Klebsiella, Pasteurella, Salmonella, Streptococcus, M. hyorhinis, M. hyopneumoniae*, Swine Influenza virus (SIAV), Porcine Reproductive and Respiratory Syndrome (PRRS) virus, Respiratory coronavirus, Porcine circovirus type 2 (PCV2), Porcine cytomegalovirus, Aujeszky's Disease, Classical swine fever, and African swine fever.

6. The method according to claim 5, wherein the respiratory pathogen is selected from the group consisting of *Actinobacillus pleuropneumoniae* (APP), *M. hyopneumoniae*, Swine Influenza, PRRS, and PCV2.

7. The method according to claim 1, wherein the respiratory pathogen is selected from the group consisting of ammonia, hydrogen sulfide, carbon dioxide and methane, dust originating from feed, fecal particles or dander, coliforms in fecal dust.

8. The method according to claim 1, wherein in step a) the sounds produced by 1 to 1000 farm animals is recorded using 1 to 4 microphones.

9. The method according to claim 1 wherein in step e) the RDI is the number of sounds caused by respiratory distress per single farm animal within 24 hours.

10. The method according to claim 1, wherein in step c) the stored data generated from the sounds produced by a group of healthy farm animals is used to filter off the background noise.

11. The method according to claim 1, wherein in step g) the stored table of respiratory pathogens comprises 1 to 10 respiratory pathogens and their corresponding RDI patterns.

12. The method according to claim 1, wherein in step a) the number of sounds caused by respiratory distress is recorded during hours of reduced activity on the farm.

13. The method according to claim 12, wherein in step a) the number of sounds caused by respiratory distress is recorded overnight.

14. The method according to claim 1, wherein in step h), the processor produces a report, indicating the predicted respiratory pathogen and optionally the underlying RDI pattern and/or transmits the report to user.

15. The method according to claim 14, wherein in step h), the processor produces a report on the screen of a computing device or in printed form.

16. The method according to claim 15, wherein the report is transmitted to the stockman or the veterinarian health professional, who is in charge of the group of farm animals.

17. A non-transitory processor readable medium having stored thereon processor executable instructions configured to cause a processor to perform each of the method steps c) to h) of claim 1.

18. A computing device for predicting a specific respiratory pathogen in a group of farm animals, the computing device comprising means to carry out the method steps b) to h) of claim 1.

19. A kit of parts comprising a computing device as claimed in claim 18; and at least one microphone connectable with said computing device.

* * * * *